(12) United States Patent
Greenawalt et al.

(10) Patent No.: US 6,957,497 B2
(45) Date of Patent: Oct. 25, 2005

(54) METHOD AND APPARATUS FOR TAKING MEASUREMENTS FOR A CUSTOM PILLOW

(75) Inventors: Kent S. Greenawalt, Roanoke, VA (US); Dwayne H. Bennett, Roanoke, VA (US)

(73) Assignee: Foot Levelers, Inc., Roanoke, VA (US)

( * ) Notice: Subject to any disclaimer, the term of this patent is extended or adjusted under 35 U.S.C. 154(b) by 0 days.

(21) Appl. No.: 10/756,656

(22) Filed: Jan. 13, 2004

(65) Prior Publication Data

US 2005/0150124 A1    Jul. 14, 2005

(51) Int. Cl.⁷ .............................................. A47G 9/00
(52) U.S. Cl. .......................................... 33/512; 5/636
(58) Field of Search ....................... 33/512, 515; 5/636, 5/655.9; 606/240

(56) References Cited

U.S. PATENT DOCUMENTS

| | | | | |
|---|---|---|---|---|
| 1,254,197 A | * | 1/1918 | Berriman ...................... | 33/512 |
| 4,756,090 A | * | 7/1988 | Pedrow ........................ | 33/512 |
| 5,060,393 A | * | 10/1991 | Silverman et al. ............ | 33/512 |
| 5,351,408 A | * | 10/1994 | Street .......................... | 33/512 |
| 5,638,564 A | | 6/1997 | Greenawalt et al. ........... | 5/636 |
| 6,415,199 B1 | * | 7/2002 | Liebermann ................. | 33/512 |

* cited by examiner

*Primary Examiner*—Christopher W. Fulton
(74) *Attorney, Agent, or Firm*—Sturm & Fix LLP

(57) ABSTRACT

A custom, therapeutic pillow is constructed based on measurements of a person's torso and head widths. A sliding caliper is used for taking the measurements. The resulting pillow is custom fitted to the patient and provides support for the head and neck when the patient is in a supine position or on their side.

15 Claims, 8 Drawing Sheets

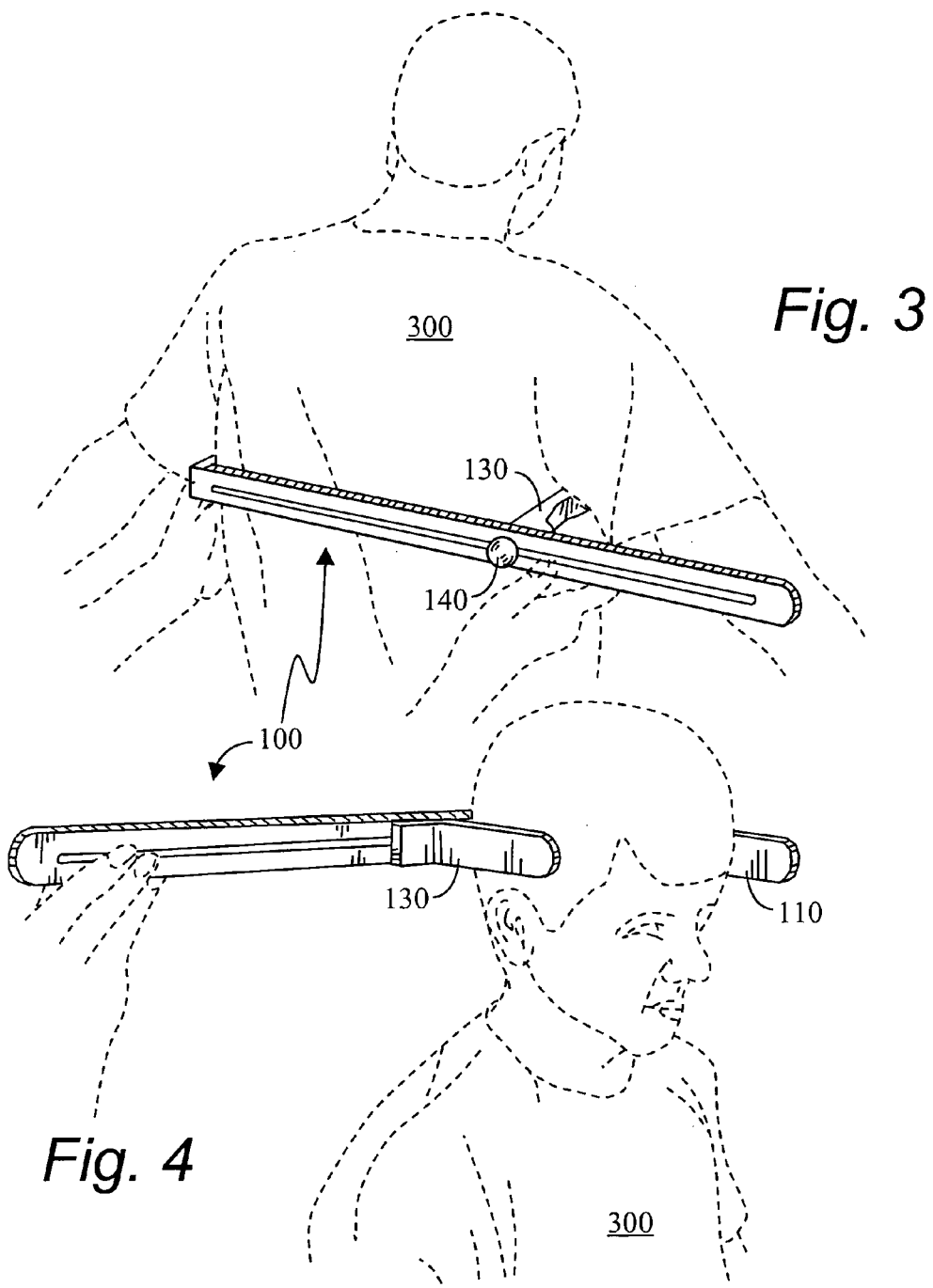

CUSTOM PILLOW LAYOUT CHART

| Torso width, θ, is 30 inches or less Base thickness: 1.25 inches (A) | | |
|---|---|---|
| θ–η (cm) | Panel size | Total height |
| LT 11 | D | 2.62 |
| 11.5-13.5 | E | 3.00 |
| 14-16.5 | F | 3.38 |
| 17-19.5 | G | 3.75 |
| 20-22.5 | H | 4.13 |
| 23-25.5 | I | 4.50 |
| 26-28.5 | J | 4.87 |
| 29+ go to (B) base | | |

| Head width, η | Torso width, θ | | | |
|---|---|---|---|---|
| | ALL | | | |
| 12-13.5 | K-2.5 x 3.25 | | | |
| 14-15 | L-3 x 3.5 | | | |
| 15.5-16 | M-3.5 x 3.75 | | | |
| 16.5+ | N-4 x 4 | | | |

| Torso width, θ, is 30.5 to 36 inches Base thickness: 1.62 inches (B) | | |
|---|---|---|
| θ–η (cm) | Panel size | Total height |
| LT 13.5 | D | 3.00 |
| 14-16.5 | E | 3.38 |
| 17-19.5 | F | 3.75 |
| 20-22.5 | G | 4.13 |
| 23-25.5 | H | 4.50 |
| 26-28.5 | I | 4.87 |
| 29-31.5 | J | 5.25 |
| 32+ go to (C) base | | |

| Head width, η | Torso width, θ | |
|---|---|---|
| | 30-33 | 33.5-36 |
| 13-14.5 | K-2.87 x 3.25 | P-2.87 x 3.75 |
| 15-16 | L-3.38 x 3.5 | Q-3.38 x 4 |
| 16.5-17.5 | M-3.87 x 3.75 | R-3.87 x 4.25 |
| 18+ | N-4.38 x 4 | S-4.38 x 4.5 |

| Torso width, θ, is above 36 inches Base thickness: 2.00 inches (C) | | |
|---|---|---|
| θ–η (cm) | Panel size | Total height |
| LT 16.5 | D | 3.38 |
| 17-19.5 | E | 3.75 |
| 20-22.5 | F | 4.13 |
| 23-25.5 | G | 4.50 |
| 26-28.5 | H | 4.87 |
| 29-31.5 | I | 5.25 |
| 32+ | J | 5.62 |

| Head width, η | Torso width, θ | |
|---|---|---|
| | 36.5-39 | 39.5+ |
| 14-15.5 | K-3.25 x 3.25 | P-3.25 x 3.75 |
| 16-17 | L-3.75 x 3.5 | Q-3.75 x 4 |
| 17.5-18.5 | M-4.25 x 3.75 | R-4.25 x 4.25 |
| 19+ | N-4.75 x 4 | S-4.75 x 4.5 |

Fig. 7

PILLOW COMPONENT DIMENSIONS CHART

| | Base | | Panel | | Rail | Center Section | | Rail | Center Section |
|---|---|---|---|---|---|---|---|---|---|
| A | 1.25x15.5x24 | D | 1.38x15.5x8 | K | 1.25x3.25x8 | 8 x 9.0 | P | 1.25x3.75x8 | 8 x 8.0 |
| B | 1.62x15.5x24 | E | 1.75x15.5x8 | L | 1.75x3.5x8 | 8 x 8.5 | Q | 1.75x4x8 | 8 x 7.5 |
| C | 2.0x15.5x24 | F | 2.13x15.5x8 | M | 2.25x3.75x8 | 8 x 8.0 | R | 2.25x4.25x8 | 8 x 7.0 |
| | | G | 2.5x15.5x8 | N | 2.75x4x8 | 8 x 7.5 | S | 2.75x4.5x8 | 8 x 6.5 |
| | | H | 2.88x15.5x8 | | | | | | |
| | | I | 3.25x15.5x8 | | | | | | |
| | | J | 3.62x15.5x8 | | | | | | |

| Item # | Component | Density lb/ft³ | ILD | Min. Height (cm) | Max. Height (cm) | Min. Width (cm) | Max. Width (cm) | Min. Length (cm) | Max. Length (cm) |
|---|---|---|---|---|---|---|---|---|---|
| 520 | Base | 3.0 | 23 | 1.25 | 2.00 | 15.50 | 15.50 | 24.00 | 24.00 |
| 510 | Panel | 1.5 | 23 | 1.38 | 3.63 | 15.50 | 15.50 | 8.00 | 8.00 |
| 530 | Rail | 3.0 | 23 | 1.25 | 3.25 | 3.25 | 4.75 | 8.00 | 8.00 |
| 540 | Center Section | 3.0 | 15 | 0.50 | 0.50 | 8.00 | 8.00 | 6.00 | 9.00 |

METHOD AND APPARATUS FOR TAKING MEASUREMENTS FOR A CUSTOM PILLOW

CROSS REFERENCE TO RELATED APPLICATIONS

This application is related to U.S. patent application Ser. No. 10/756,655 filed Jan. 13, 2004 entitled CUSTOM THERAPEUTIC PILLOW.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

This invention relates generally to custom pillows, and more particularly to a scheme for taking measurements for a custom, therapeutic pillow, designed to be placed under the head and neck of a patient lying in a supine position.

2. Background Art

Because approximately one-third of all human existence is spent in a supine position, innovators in posture or cervical pillows have long continued to develop new designs of this type of pillow. Such a pillow supports the head and spine, and in particular, the neck vertebrae in the most normal, comfortable and unstressed position, thereby aiding in relieving stress in the cervical or neck portion of the upper spine, and for promoting proper posture.

Prior art in the area of such pillows have used a combination of firm and soft portions of a pillow in varied arrangements, but which have either resulted in a flattening of the spinal column, or in exaggerating the curvature thereof. Furthermore, such prior art efforts do not provide the variety of therapeutic uses of the pillow custom for each individual person.

A therapeutic pillow was disclosed in U.S. Pat. No. 5,638,564 having a base topped by three additional cushions. The component parts have varying firmnesses. The pillow disclosed in U.S. Pat. No. 5,638,564 is not a custom pillow in that the pillow is not fit to a patient based on measured data from that patient.

There is, therefore, a need for a pillow measuring system for the production of a custom, therapeutic pillow that provides the least stress on the body for relaxing, therapeutic rest.

BRIEF SUMMARY OF THE INVENTION

An object of this invention is to provide a measurement system, the result of which is a therapeutic pillow, customized as to fit for a particular patient. The construction of this pillow enables it to be used over a period of years for the treatment of conditions such as: improper cervical spine alignment, whiplash, cervical strains and sprains, tension headaches, and neck or shoulder problems.

A related object of the present invention is a method for taking accurate measurements to produce a custom therapeutic pillow that effectively provides support positions for the head, neck and shoulders of a person, whether lying supine or on the side. Thus a new and improved custom therapeutic pillow is produced by this measurement method and apparatus wherein the patient may lie back with the patient's head in a cavity; and as well, the patient may roll over and have the neck and head appropriately supported.

An additional object of this invention is to provide a sliding caliper for making rapid, accurate measurements with which to design a custom therapeutic pillow.

The novel features which are believed to be characteristic of this invention, both as to its organization and method of operation together with further objectives and advantages thereto, will be better understood from the following description considered in connection with the accompanying drawings in which a presently preferred embodiment of the invention is illustrated by way of example. It is to be expressly understood however, that the drawings are for the purpose of illustration and description only and not intended as a definition of the limits of the invention.

BRIEF DESCRIPTION OF THE SEVERAL VIEWS OF THE DRAWINGS

FIG. 3 is a perspective view of a torso measurement being taken with the sliding calipers;

FIG. 4 is a perspective view of a head width measurement being taken with the sliding calipers;

FIG. 7 is a first set of tables used as tools to determine dimensions of the custom, therapeutic pillow;

DETAILED DESCRIPTION OF THE INVENTION

Figure 1:
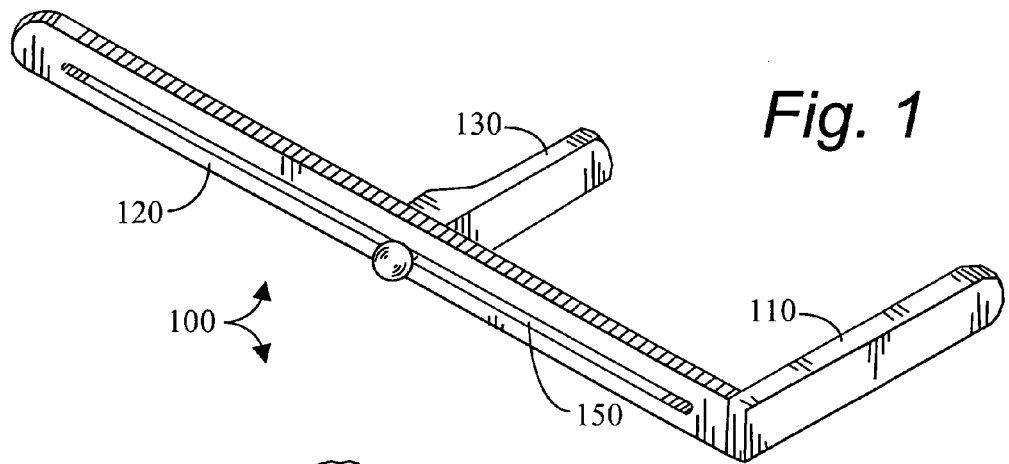
FIG. 1 is a perspective view of a sliding caliper for taking the measurements for a custom, therapeutic pillow.
Figure 2:
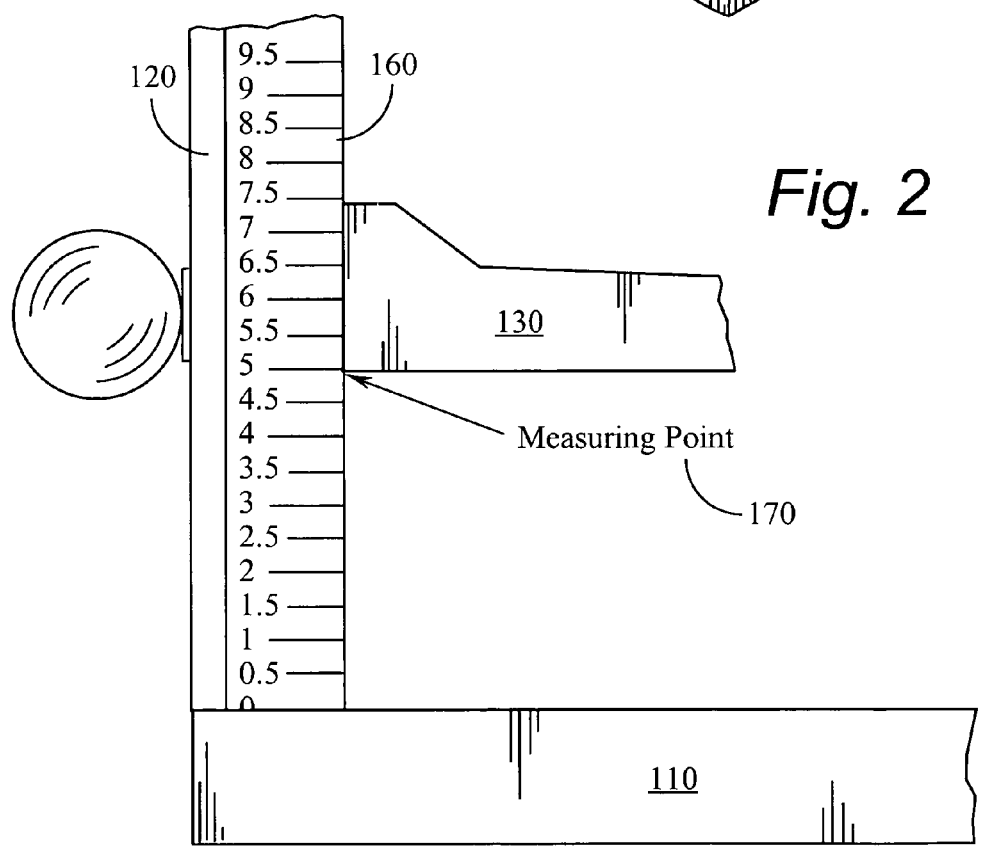
FIG. 2 is a close-up of a measuring point on the sliding caliper.

Precise measurements for producing a custom, therapeutic pillow 500 (see FIGS. 5–6) are made by the sliding caliper 100 shown in the preferred embodiment in FIGS. 1 and 2. A fixed jaw 110 is firmly affixed to a ruler 120. A sliding jaw 130 is slidably attached to the ruler 120 by a screw 140 engaging a slot 150 in the ruler. The screw 140 may be tightened to hold the sliding jaw 130 in a fixed position on the ruler 120. The ruler 120 is fitted with a scale 160 to which a location of the sliding jaw 130 is compared as shown in FIG. 2. The measurement point 170 is the shown as an inside edge of the sliding jaw 130.

Possible materials for constructing the sliding caliper 100 include wood, plastic, and a variety of metals. The present invention is not limited to any given material or set of materials.

The sliding caliper 100 is shown in use in FIGS. 3–4 which illustrate the method of measurements for producing the custom, therapeutic pillow 500. In FIG. 3, the sliding caliper 100 is being used to measure a width of a patient 300 across the patient's torso, just under the arms. The sliding caliper 100 is first spread apart so the distance between the jaws 110, 130 is greater than the patient's 300 torso. The sliding caliper 100 is placed into position as shown in FIG. 3 whereupon the sliding jaw 130 is slid toward the fixed jaw 110 until the two jaws 110, 130 make contact with the patient's 300 sides. The screw 140 is tightened to maintain the position of the sliding jaw 130 and the scale read. This measurement is referred to as "torso width, $\theta$" in the tables of FIG. 7 and is in centimeters (cm) in those table, although this invention is not limited to a specific system of units.

In FIG. 4, the sliding caliper 100 is shown in use for measuring the patient's 300 head width just above the ears. The sliding caliper 100 is used similarly to that explained for the torso width measurement. This last measurement is called "head width, $\eta$" in the table of FIG. 7.

Figure 5:
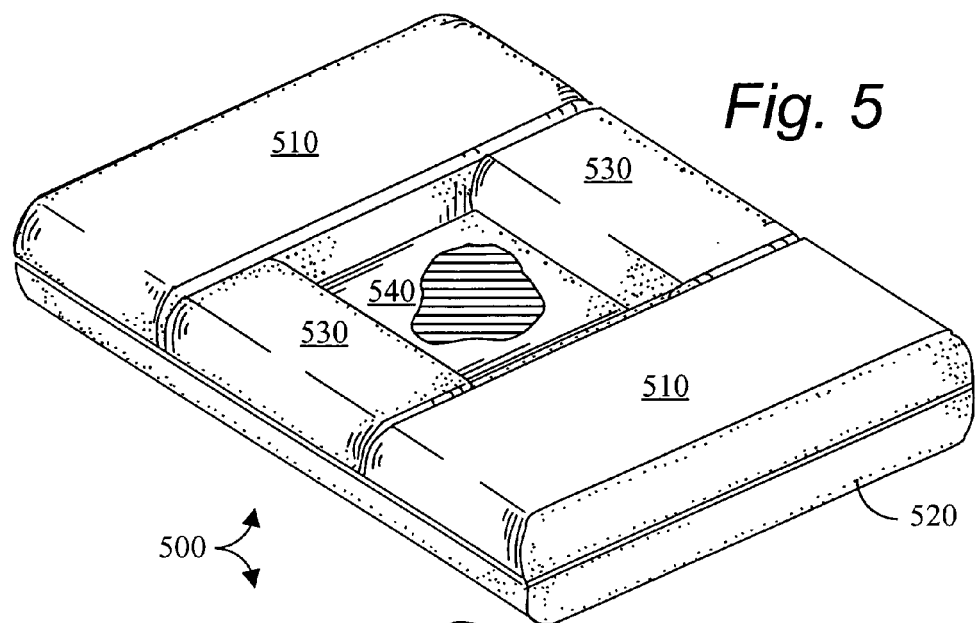
FIG. 5 is a first perspective view of a custom, therapeutic pillow.
Figure 6:
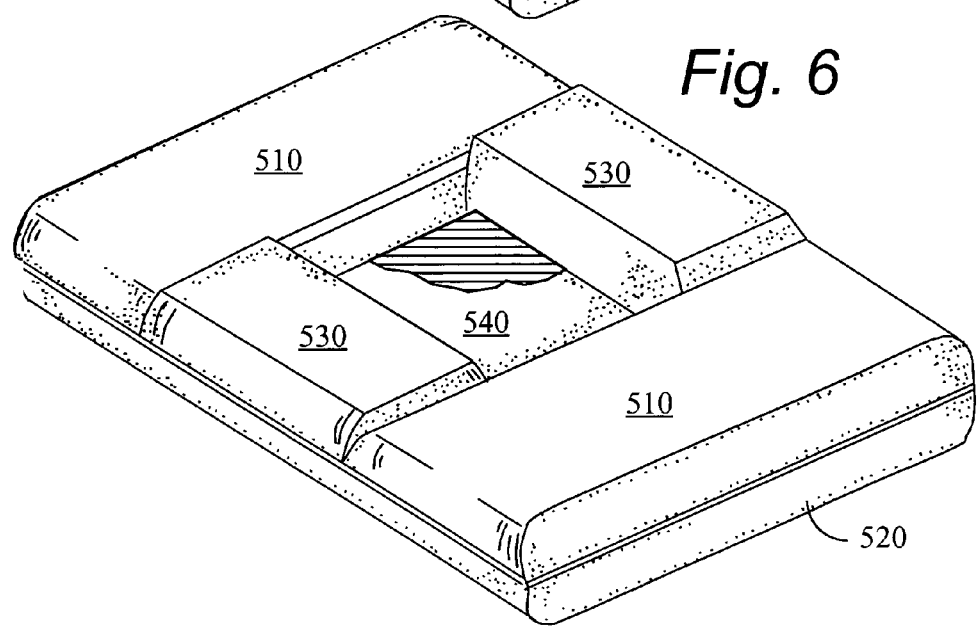
FIG. 6 is a second perspective view of a custom, therapeutic pillow.

The custom, therapeutic pillow 500 of this invention is shown in perspective in FIGS. 5 and 6. The main components of the custom, therapeutic pillow 500 are the two side panels 510, the base 520, and the two rails 530. All these components 510, 520, 530 are made of urethane foam in the preferred embodiment. As seen in FIG. 5, the two rails 530 may be thicker than the two side panels 510. The center of the base comprises a Visco elastic insert 540. The indentation made by the two side panels 510 and the two rails 530 is made to receive the patient's 300 head.

Figure 11:
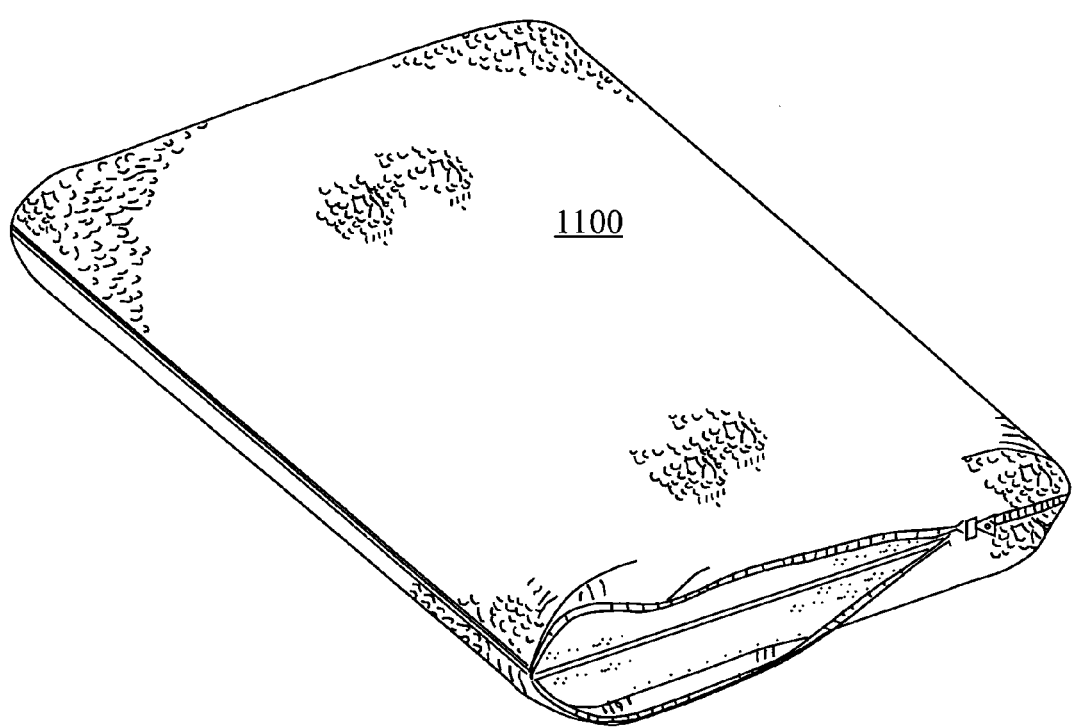
FIG. 11 is a perspective view of the custom, therapeutic pillow in a pillow cover.

A washable outer ticking 1100 (see FIG. 11) covers the combined members 510, 520, 530, and 540.

Figure 10:
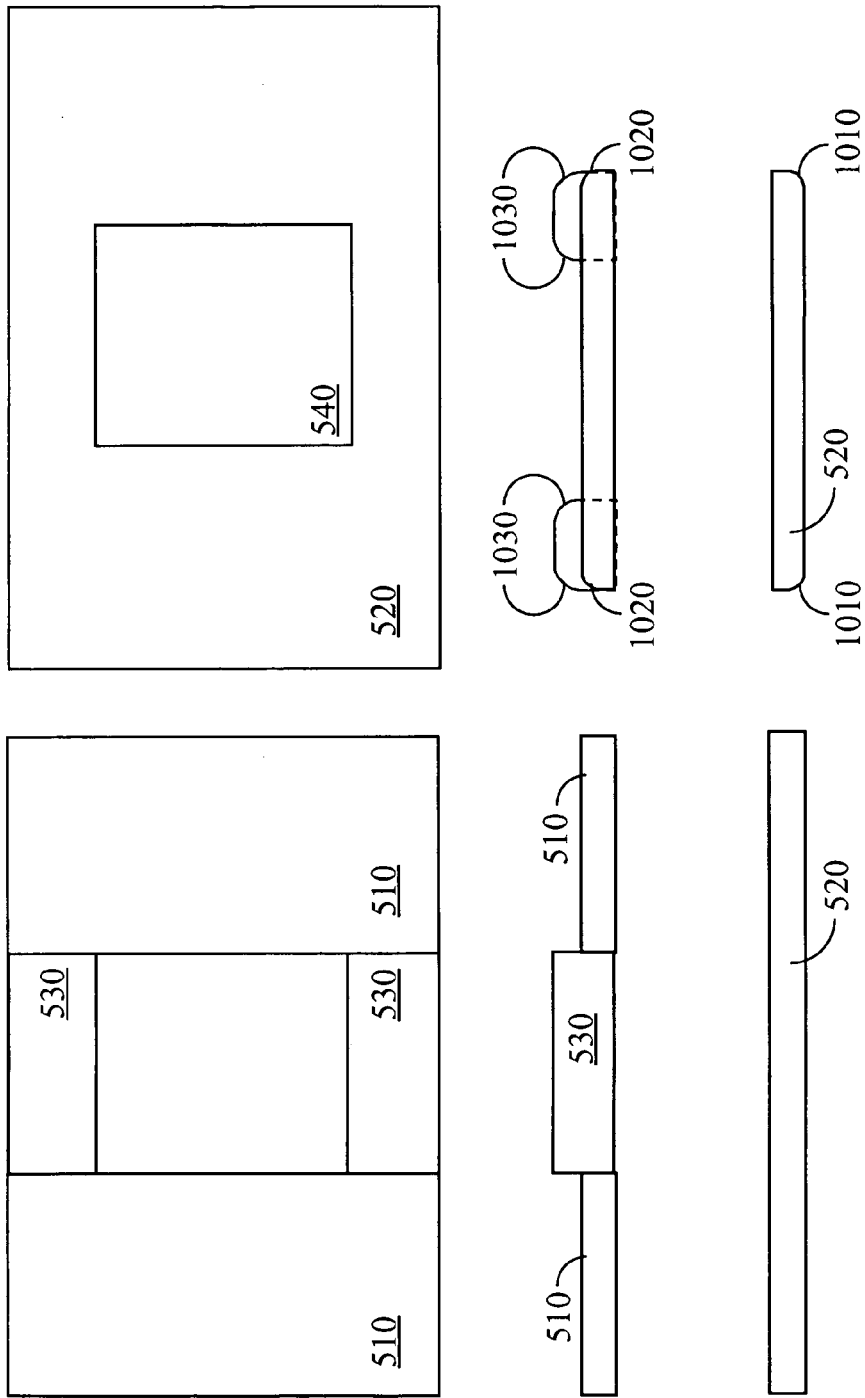
FIG. 10 is a second working drawing of the custom, therapeutic pillow.

More particularly, and referring to FIGS. 5, 6, and 10, the base 520 has a substantially planar upper surface. The lower corners of the base's 520 long sides have rounded edges 1010. A center of the base 520 is open or recessed to receive the center section 540.

Placed on top of the base 520 and bonded to the base 520 are the panels 510 and rails 530. The panels 510 and rails 530 each have a substantially planar lower surface to which the base 520 is bonded.

The upper corners of the short sides of the panels 510 have rounded edges 1020 corresponding with the rounded edge 1010 of the base 520.

Likewise, the upper corners of the long sides of the rails 530 have rounded edges 1030 corresponding with the rounded edge 1010 of the base 520 and an inner cavity created by the panels 510 and the rails 530 and floored by the center section 540.

Figures 8, 12:
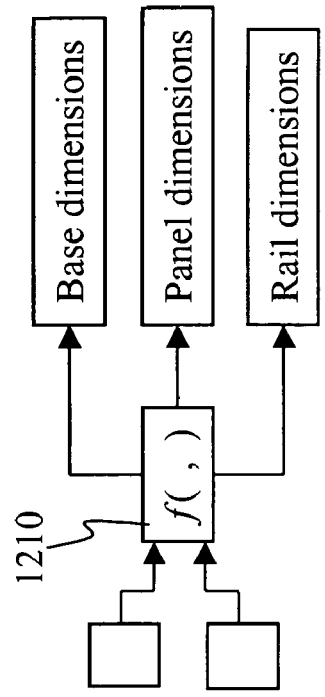
FIG. 8 is a second set of tables used as tools to determine dimensions and foam characteristics of the custom, therapeutic pillow.
FIG. 12 is a block diagram showing a computing function for determining dimensions for the custom, therapeutic pillow.

The process for measuring and creating a custom pillow is as follows. The torso width, $\theta$, and head width, $\eta$, are measured as described, above. From the torso width, $\theta$, the appropriate table is chosen from FIG. 7 as indicated at the top of each table. If the torso width is less than or equal to 30 cm, the left-hand table is used. For torso widths in the range of 30.5 to 36 cm, the center table is used. Larger torso widths require the use of the right-hand table. In the second row of each table, immediately under the shoulder width range, is the base thickness in inches, and a letter (A, B, C) designating which base is to be used. The base letter and base dimensions, in inches, are shown in FIG. 8 in the left-hand two columns.

In the third row, immediately below the base thickness, the left hand column is headed "$\theta-\eta$ (cm)." The head width, $\eta$, is subtracted from the torso width, $\theta$, and the result compared with the ranges in this left hand column. By following the resulting row across to the right, the panel letter designation (D-J) is determined, and the total height of the pillow is known from the center and right-hand columns, respectively. Once the panel letter is determined, the center table in FIG. 8 may be used to ascertain the overall dimensions of the panels to be used.

We now use the lower half of the three tables in FIG. 7, under the heading "Torso width, $\theta$." From the two measurements already taken, torso width, $\theta$, and head width, $\eta$, the rail size is determined. Ranges of head widths, $\eta$, in cm, are shown in the left-hand column. Ranges of torso widths, $\theta$, in cm, are shown in the row immediately under the heading "Torso width, $\theta$." Choosing the appropriate row based on head widths, $\eta$, and column based on torso widths, $\theta$, results in a rail letter (K-S without "O") and rail cross-section dimensions (the height includes the base thickness) in inches. The overall rail dimensions, in inches, are shown in the right-hand table of FIG. 8.

For use on a waterbed, a soft mattress or a mattress more than six (6) years old, it is recommended in the preferred embodiment that all components 510, 520, 530 of the custom, therapeutic pillow 500 be reduced by one letter.

A final step is to ascertain that the rail thickness is not more than one (1) inch greater than the panel thickness. Should the rail thickness prove more than 1" greater than the panel thickness, the rail thickness would be modified to reduce it to the panel thickness plus one (1) inch. No change is made to the other rail dimensions or the panel dimensions.

At this point, all dimensions of all parts of the custom pillow 500 are known.

To use an example, a patient 300 will be using their custom, therapeutic pillow on a new mattress which is not a waterbed mattress. The patient's 300 torso width, $\theta$, measures 32 cm and head width, $\eta$, measures 15 cm. The center table in FIG. 7 is used because $30.5 \leq 32 \leq 36$. Thus the base letter is "B" and will be 1.62 inches thick. Looking at the left-hand table in FIG. 8, we see the base will be 1.62×15.5×24, all in inches. Taking the head width, $\eta$, from the torso width, $\theta$, results in 17 cm (32–15=17). Thus, the sixth ($6^{th}$) row from the top of the center table in FIG. 7 is used because the range of $\theta-\eta$ is 17–19.5 cm. The correct panel letter is "F" and the thickness of the panel plus the base will be 3.75 inches. Using FIG. 8, we determine the panels will measure 2.13×15.5×8, all in inches, based on panel letter "F."

The next step is to move into the lower part of the center table in FIG. 7 to determine the appropriate rail size. Knowing the head width, $\eta$, is in the range 15–16 cm and the torso width, $\theta$, lies in the range 30–33 cm, we determine the rail letter to be "L." The rail dimensions are found in the right-hand table in FIG. 8, where we find a rail with a letter "L" is 1.75×3.5×8, all in inches. Finally, we compare the rail thickness, 1.75" to the panel thickness, 2.13" to ascertain that the rail is not more than 1" thicker than the panel. In this case it is not. If the rail had been more than 1" thicker than the panel, the thickness of the rail would be modified to the panel thickness plus one (1) inch.

Figure 9:
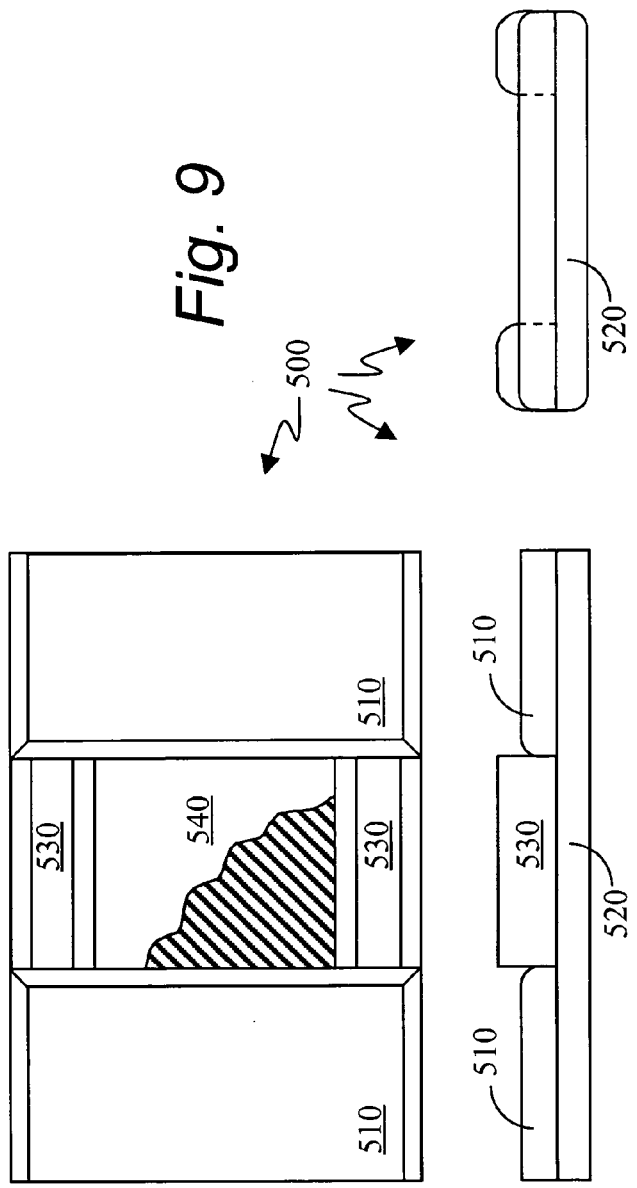
FIG. 9 is a first working diagram of the custom, therapeutic pillow with a table of foam densities and dimension ranges.

Additional data are given in the table of FIG. 9. The values given in the column headed "Density, lb/ft$^3$," are the densities of the foam used for the four components 510, 520, 530, 540. Firmness generally increases with increased density. In the column headed "ILD," the Indent Load Deflection (ILD) of the components 510, 520, 530, 540 is given. Additionally, maximum and minimum dimension ranges are given for each of the components 510, 520, 530, 540.

A flow diagram with the values of torso width, $\theta$, and head width, $\eta$, being entered into a computing function 1210 is shown in FIG. 12. The dimensions for the base, panels, and rails are outputted from the computing function 1210. Such a computing function may be effected by software in a personal or mainframe computer, handheld calculator, or a dedicated calculating unit, perhaps built into the sliding calipers 100.

The above embodiment is the preferred embodiment, but this invention is not limited thereto. It is, therefore, apparent that many modifications and variations of the present invention are possible in light of the above teachings. It is, therefore, to be understood that within the scope of the appended claims, the invention may be practiced otherwise than as specifically described.

We claim:

1. A method of constructing a custom, therapeutic pillow comprising a base and at least one panel, the method comprising:
    (a) measuring a torso width, $\theta$, of a patient just under said patient's arms;
    (b) measuring a head width, $\eta$, of a patient just above said patient's ears;
    (c) dimensioning a base thickness of the custom, therapeutic pillow as a function of a range of the patient's torso width, $\theta$; and
    (d) dimensioning a panel size of the custom, therapeutic pillow as a function of the patient's torso width, $\theta$, and head width, $\eta$.

2. The method of claim 1 wherein a sliding caliper is used to measure the patient's torso width, $\theta$.

3. The method of claim 1 wherein a sliding caliper is used to measure the patient's head width, $\eta$.

4. The method of claim 1 wherein a range of torso widths is determined in which the patient's torso width, $\theta$, lies for determining the base dimensions.

5. The method of claim 1 wherein dimensioning a panel size of the custom, therapeutic pillow comprises:
    calculating a difference by subtracting the patient's head width, $\eta$, from the patient's torso width, $\theta$, and using said difference to determine the panel dimensions.

6. The method of claim 1 additionally comprising:
    (a) determining a range of torso widths in which the patient's torso width, $\theta$, lies;
    (b) determining a range of head widths in which the patient's head width, $\eta$, lies; and
    (c) using the range of torso widths and the range of head widths to determine the rail dimensions.

7. A method of constructing a custom, therapeutic pillow comprising at least one panel, the method comprising:
    (a) measuring a head width, $\eta$, of a patient just above said patient's ears;
    (b) dimensioning a panel size of the custom, therapeutic pillow based on a range of the patient's head width, $\eta$.

8. The method of claim 7 wherein a sliding caliper is used to measure the patient's head width, $\eta$.

9. A system for producing a custom, therapeutic pillow comprising a base, rails, panels, and a center section, the system comprising:
    (a) a sliding caliper for measuring a torso width, $\theta$, and a head width, $\eta$, of a patient;
    (b) an input unit into which the torso width, $\theta$, and a head width, $\eta$ are inputted;
    (c) a computing function connected to the input unit to receive values of the torso width, $\theta$, and head width, $\eta$; and
    (d) an output unit, connected to the computing function and from which dimensions for the base, rails, panels, and center section are outputted.

10. A method of constructing a custom, therapeutic pillow comprising a base, the method comprising:
    (a) measuring a torso width, $\theta$, of a patient just under said patient's arms; and
    (b) dimensioning a base thickness of the custom, therapeutic pillow as a function of a range of the patient's torso width, $\theta$.

11. The method of claim 10 wherein a sliding caliper is used to measure the patient's torso width, $\theta$.

12. The method of claim 10 wherein a range of torso widths is determined in which the patient's torso width, $\theta$, lies for determining the base dimensions.

13. The method of claim 10 additionally comprising:
    (a) measuring a head width, $\eta$, of a patient just above said patient's ears;
    (b) calculating a difference by subtracting the patient's head width, $\eta$, from the patient's torso width, $\theta$, and using said difference to determine the panel dimensions.

14. The method of claim 10 additionally comprising:
    (a) measuring a head width, $\eta$, of a patient just above said patient's ears;
    (b) determining a range of torso widths in which the patient's torso width, $\theta$, lies;
    (c) determining a range of head widths in which the patient's head width, $\eta$, lies; and
    (d) using the range of torso widths and the range of head widths to determine the rail dimensions.

15. A method of constructing a custom, therapeutic pillow, the method comprising the steps of:
    (a) measuring a torso width, $\theta$, of a patient just under said patient's arms;
    (b) dimensioning the custom, therapeutic pillow based on the patient's torso width, $\theta$;
    (c) measuring a head width, $\eta$, of a patient just above said patient's ears;
    (d) calculating a difference by subtracting the patient's head width, $\eta$, from the patient's torso width, $\theta$, and using said difference to determine panel dimensions.

* * * * *